(12) United States Patent
Hashizaki et al.

(10) Patent No.: US 11,004,551 B2
(45) Date of Patent: May 11, 2021

(54) SLEEP IMPROVEMENT SYSTEM, AND SLEEP IMPROVEMENT METHOD USING SAID SYSTEM

(71) Applicant: OMRON Corporation, Kyoto (JP)

(72) Inventors: Masanori Hashizaki, Nara (JP); Junya Yamamoto, Kyotanabe (JP); Hiroshi Nakajima, Kyoto (JP)

(73) Assignee: OMRON Corporation, Kyoto (JP)

( * ) Notice: Subject to any disclaimer, the term of this patent is extended or adjusted under 35 U.S.C. 154(b) by 215 days.

(21) Appl. No.: 15/528,782

(22) PCT Filed: Dec. 17, 2015

(86) PCT No.: PCT/JP2015/085367
§ 371 (c)(1),
(2) Date: May 23, 2017

(87) PCT Pub. No.: WO2016/104325
PCT Pub. Date: Jun. 30, 2016

(65) Prior Publication Data
US 2017/0312477 A1 Nov. 2, 2017

(30) Foreign Application Priority Data

Dec. 25, 2014 (JP) .............................. JP2014-262335

(51) Int. Cl.
*G16H 20/00* (2018.01)
*A61B 5/16* (2006.01)
(Continued)

(52) U.S. Cl.
CPC ............... *G16H 20/00* (2018.01); *A61B 5/16* (2013.01); *A61B 5/4812* (2013.01);
(Continued)

(58) Field of Classification Search
None
See application file for complete search history.

(56) References Cited

U.S. PATENT DOCUMENTS

2009/0112069 A1 4/2009 Kanamori et al.
2010/0099954 A1* 4/2010 Dickinson ............ A61B 5/0006
600/300
(Continued)

FOREIGN PATENT DOCUMENTS

CN 103415248 A 11/2013
CN 104053397 A 9/2014
(Continued)

OTHER PUBLICATIONS

ResMed. (May 23, 2012). Omron Launches Sleep Monitor With ResMed Technology [Press release]. Retrieved Mar. 27, 2019, from http://investors.resmed.com/investor-relations/events-and-presentations/press-releases/press-release-details/2012/Omron-Launches-Sleep-Monitor-With-ResMed-Technology/default.aspx.*
(Continued)

*Primary Examiner* — Jerry-Daryl Fletcher
*Assistant Examiner* — Daniel E Lane
(74) *Attorney, Agent, or Firm* — Metrolex IP Law Group, PLLC

(57) ABSTRACT

A sleep improvement system includes a lifestyle pattern generator configured to generate a lifestyle pattern from at least one of sleep information about sleep of a user, lifestyle information about the user, and living condition information about the user.

6 Claims, 5 Drawing Sheets

(51) Int. Cl.
    *A61B 5/00*     (2006.01)
    *A61M 21/02*     (2006.01)
    *G09B 19/00*     (2006.01)
    *G06N 7/00*     (2006.01)
    *A61M 21/00*     (2006.01)

(52) U.S. Cl.
    CPC ........... *A61B 5/4815* (2013.01); *A61M 21/02* (2013.01); *G06N 7/005* (2013.01); *G09B 19/00* (2013.01); *A61M 2021/0011* (2013.01)

(56) References Cited

U.S. PATENT DOCUMENTS

| | | | | |
|---|---|---|---|---|
| 2011/0015495 | A1* | 1/2011 | Dothie | G16H 10/60 600/300 |
| 2011/0230790 | A1 | 9/2011 | Kozlov | |
| 2012/0238800 | A1* | 9/2012 | Naujokat | A61B 5/0402 600/26 |
| 2013/0310662 | A1 | 11/2013 | Tsutsumi et al. | |
| 2014/0276245 | A1* | 9/2014 | Tsutsumi | A61B 5/1118 600/595 |
| 2014/0347366 | A1 | 11/2014 | Emori et al. | |
| 2016/0151603 | A1* | 6/2016 | Shouldice | H04R 3/00 600/28 |

FOREIGN PATENT DOCUMENTS

| | | |
|---|---|---|
| EP | 2278508 A1 | 1/2011 |
| JP | 2007-034744 A | 2/2007 |
| JP | 2007-319238 A | 12/2007 |
| JP | 2009-106681 A | 5/2009 |
| JP | 2011-258137 A | 12/2011 |
| JP | 2012-058939 A | 3/2012 |
| JP | 2013-045336 A | 3/2013 |
| JP | 2014-030494 A | 2/2014 |
| JP | 2014-071787 A | 4/2014 |
| JP | 2014-215691 A | 11/2014 |
| WO | 2010/048310 A1 | 4/2010 |
| WO | 2015/006364 A2 | 1/2015 |

OTHER PUBLICATIONS

The extended European search report dated Dec. 13, 2017 in a counterpart European Patent application.
The Japanese office action letter dated Oct. 23, 2018 in a counterpart Japanese patent application.
The Communication pursuant to Article 94(3) EPC dated Mar. 5, 2020 in a related European patent application.
The Office Action dated Mar. 24, 2020 in a related Chinese patent application.

* cited by examiner (a)

(b)

(c)

SLEEP IMPROVEMENT SYSTEM, AND SLEEP IMPROVEMENT METHOD USING SAID SYSTEM

CROSS-REFERENCE TO RELATED APPLICATIONS

This application claims priority to Japanese Patent Application No. 2014-262335 filed with the Japan Patent Office on Dec. 25, 2014, the entire contents of which are incorporated herein by reference. The cited documents are incorporated herein by reference in its entirety.

TECHNICAL FIELD

The present invention relates to a system for improving sleep and a method thereof. Hereinafter, a person who works on sleep improvement is generally referred to as a user.

BACKGROUND ART

Conventionally, there has been known a technology that advises the user to be able to obtain a good sleep state.

For example, Patent Document 1 discloses a system that calculates information about an active state, in which the user can obtain the good sleep state, and informs the user of the calculated information about the active state.

Patent Document 2 discloses a sleep state evaluation device that detects the user's sleep state, determines and evaluates the sleep state and a life rhythm based on the sleep state, and advises the user to improve the sleep state.

On the other hand, Patent Document 3 discloses a technology of estimating an optimal reporting period of time from user's life pattern with respect to the information provided to the user.

PRIOR ART DOCUMENTS

Patent Documents

Patent Document 1: Japanese Unexamined Patent Publication No. 2014-30494
Patent Document 2: Japanese Unexamined Patent Publication No. 2013-45336
Patent Document 3: Japanese Unexamined Patent Publication No. 2014-71787

SUMMARY OF THE INVENTION

Problems to be Solved by the Invention

For example, in the conventional technology of Patent Document 1, the evaluation is performed based on such one piece of data as a number of steps, and the evaluation is performed by only one side. That is, because cognitive and psychological states of the user or living conditions such as a weekday and a holiday are not reflected, the user neither easily practices nor is sufficiently satisfied with the provided improvement information.

In the technology of Patent Document 2 associated with the sleep improvement, quality of the sleep is evaluated with information about a target group as a reference, but the reference is not always applicable to an individual. Additionally, the advice provided to the user must be a uniform content based on an obtained score. For these reasons, there is a possibility that the information sufficiently satisfying the user is not always provided.

As to timing of providing information such as the advice, conventionally the reporting time is decided by the life pattern of the user such as Patent Document 3, but the reporting time is not decided in consideration of a change in the user's living conditions.

In view of the aforementioned circumstances, an object of the present invention is to provide a sleep improvement system and a sleep improvement method, which can enhance ease of reception of the information about the sleep improvement and encourage the user to improve the sleep in consideration of a problematic issue of user's sleep, an influence of an environmental change on the user, and a lifestyle or living conditions of the user.

Means for Solving the Problem

According to one aspect of the present invention, a sleep improvement system includes a lifestyle pattern generator configured to generate a lifestyle pattern from at least one of sleep information about sleep of a user, lifestyle information about the user, and living condition information about the user.

As used herein, the lifestyle information means information indicating a lifestyle that is of a daily routine behavior.

The living condition information means information indicating a user situation, for example, a busy life, a frequent business trip, a long vacation, and an irregular life such as a night duty.

In the sleep improvement system according to the present invention, the sleep information may include at least one of a wake-up time, a time in bed, a total sleep time, a total time in bed, sleep efficiency, a wake after sleep onset, a number of awakenings after sleep onset, and sleep latency.

The wake-up time means time the user wakes up, the time in bed means time the user goes to bed, the total sleep time means a total time for which the user actually sleeps in one night, and the total time in bed means a total time the user is in bed in one night.

The sleep efficiency means a ratio of a sleeping time to time for which the user is in the bed, and the sleep efficiency is given by the following equation (1).

$$\text{sleep efficiency [\%]} = (\text{total sleep time}/\text{total time in bed}) \times 100 \quad (1)$$

The wake after sleep onset means time for which the user awakes in the sleep, the number of awakenings after sleep onset means a frequency at which the user awakes in the sleep, and the sleep latency means time which it takes for the user to fall asleep since the time in bed.

The sleep improvement system may further include: a sleep improvement message type selector configured to select a type of a sleep improvement message based on the generated lifestyle pattern; a sleep improvement message timing selector configured to select timing of outputting the selected type of the sleep improvement message; and a sleep improvement message outputting unit configured to output the selected type of the sleep improvement message in the selected timing.

Effect of the Invention

According to the configuration of the sleep improvement system of the present invention, the lifestyle pattern is generated from at least one of the sleep information, the user lifestyle information, and the living condition information about the user, so that the system can be constructed in consideration of such indexes depending on an individual as the problematic issue of user's sleep, the influence of the environmental change on the user, and the lifestyle or living conditions of the user.

For the configuration including the sleep improvement message type selector, the sleep improvement message timing selector, and the sleep improvement message outputting unit, the type of the provided message or the timing of transmitting the message can be changed in consideration of the indexes.

Resultantly, the ease of reception can be enhanced when the user receives the message, and the user can be encouraged to efficiently improve the sleep.

MODE FOR CARRYING OUT THE INVENTION

[Configuration of Sleep Improvement System According to an Embodiment]

Figure 1:
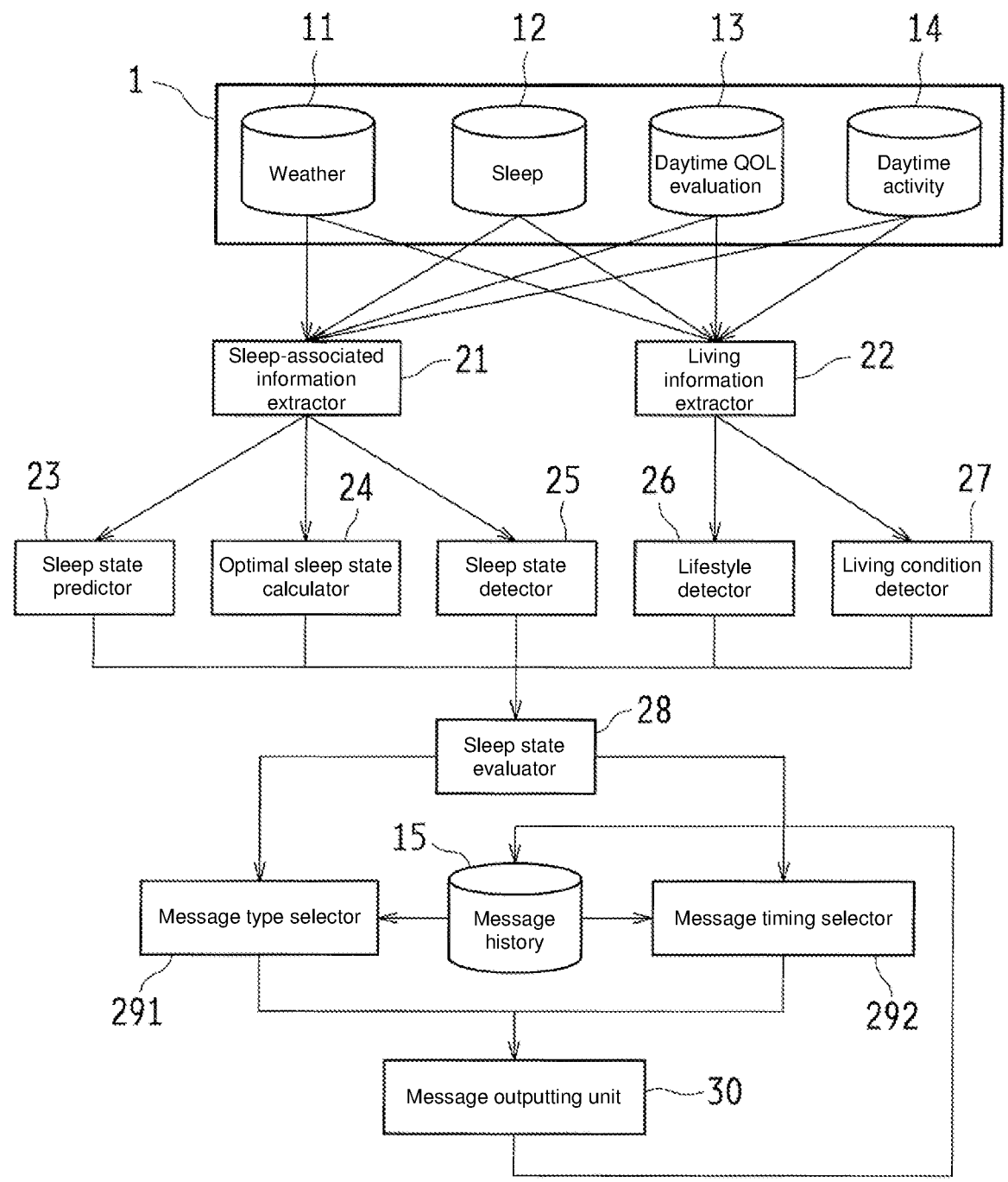
FIG. 1 is a block diagram illustrating a configuration of a sleep improvement system according to an embodiment of the present invention.

FIG. 1 is a block diagram illustrating a configuration of a sleep improvement system according to an embodiment of the present invention.

The sleep improvement system of the embodiment is provided with a database 1 including a weather information database 11, a sleep information database 12, a daytime quality-of-life (QOL) evaluation database 13, and a daytime activity information database 14.

Environment information obtained with a system that obtains external environment information and environment information obtained with a device that obtains indoor environment information are stored in the weather information database 11. Examples of the environment information include, but not limited to, temperature, humidity, and illuminance, which vary depending on a weather or a season.

Sleep information obtained with, for example, a sleep meter is stored in the sleep information database 12. Examples of the sleep information include a wake-up time, a time in bed, a total sleep time, a total time in bed, sleep efficiency, wake after sleep onset, a number of awakenings after sleep onset, and sleep latency.

QOL evaluation data indicating evaluation of daytime quality of life of the user is stored in the daytime QOL evaluation database 13. For example, a subjective questionnaire and a stress check result performed in an office or the like may be stored as the daytime QOL evaluation data. These pieces of data are used as not only the daytime QOL evaluation of the user but also an index indicating the cognitive and psychological states of the user. The user's living conditions are obtained using the daytime QOL evaluation database 13.

A user's behavior including daytime activity of the user, namely, behavior information, such as a number of steps and a movement time, which is obtained with activity information measurement device such as an activity meter and a 24-hour wearable terminal, is stored in the daytime activity information database 14.

Past data including a day when the sleep improvement system is used (also referred to as that day) is stored in each database.

The sleep improvement system also includes a sleep-associated information extractor 21 that extracts sleep-associated information from the database and a living information extractor 22 that extracts life-associated information from the database.

The sleep improvement system also includes a sleep state predictor 23 that predicts the sleep state based on the information extracted with the sleep-associated information extractor 21, an optimal sleep state calculator 24 that calculates the optimal sleep state based on the information extracted with the sleep-associated information extractor 21, a sleep state detector 25 that detects the sleep state based on the information extracted with the sleep-associated information extractor 21, a lifestyle detector 26 that detects the lifestyle based on the information extracted with the living information extractor 22, and a living condition detector 27 that detects the living conditions based on the information extracted with the living information extractor 22.

The sleep improvement system also includes a sleep state evaluator 28 that evaluates the actual sleep of the user, a message type selector 291 that produces a content of a sleep improvement message (hereinafter, referred to as a message) based on an evaluation result of the sleep state evaluator 28 and selects a type of the message, a message timing selector 292 that selects message transmission timing, a message outputting unit 30 that outputs the message selected with the message type selector 291 in timing selected with the message timing selector 292, and a message history database 15 in which an output history of the message is stored.

The sleep state evaluator 28 produces a lifestyle pattern based on the pieces of the sleep information detected with the sleep state detector 25, the lifestyle information detected with the lifestyle detector 26, and the living condition information detected with the living condition detector 27, calculates a deviation between the sleep information and the optimal sleep information of that day based on the pieces of information from the sleep state predictor 23, the optimal sleep state calculator 24, and the sleep state detector 25, which will be described later, and calculates a deviation between a predictive value of each of the time in bed, wake-up time, and sleep time, which are predicted with the sleep state predictor 23 and the optimal sleep information. The sleep state evaluator 28 also performs evaluation based on a result of the deviation calculation and the lifestyle pattern.

In the case that the lifestyle pattern is produced, although the sleep information is necessary, the lifestyle information and the living condition information are not always necessary, but only at least one of the lifestyle information and the living condition information is necessary.

For example, the user's living conditions can be obtained when a work day and a non-work day are estimated using the time in bed and wake-up time, which are of the sleep information. In this case, the non-work is estimated based on regularity of the wake-up time and time in bed, which are of the sleep information about the user, and the day when a variation is large in the wake-up time or time in bed is estimated to be the non-work day, and the day when a variation is small in the wake-up time or time in bed is estimated to be the work day.

Additionally, busyness can be estimated from the sleep information. In this case, a degree of busyness is previously classified based on a length of user's sleep time, and which one of the degrees the current busyness belongs to is detected based on the classification. Therefore, the current busyness of the user is estimated. For example, in the case that the length of time in bed (TIB: time for which the user spends in bed) places in top 10%, currently the user is estimated to be in a busy period. The top 10% means ranks including 10% of a total of TIB data in a period of the user when the TIB data is counted from the shortest one in the ascending order of the length of TIB data. For example, in the case that 60 pieces of data exist as 60-day data, the data having the shortest TIB is set to a first place, and the TIB data is ranked in the ascending order of the length of TIB data. In this case, the current TIB is compared to 10% of 60, namely, the TIB data ranked sixth, and currently the user is estimated to be in the busy period when the current TIB is ranked within the sixth place.

Thus, the lifestyle information such as information about the routine work of the user or the living condition information such as the busyness can be obtained from the sleep information without the lifestyle information or living condition information.

The busyness or motivation for the maintenance and improvement of the lifestyle can also be estimated from a measurement frequency of the device.

The sleep state predictor 23 analyzes a relationship between the sleep and the temperature based on the past sleep information about the user and temperature data.

Figure 3:
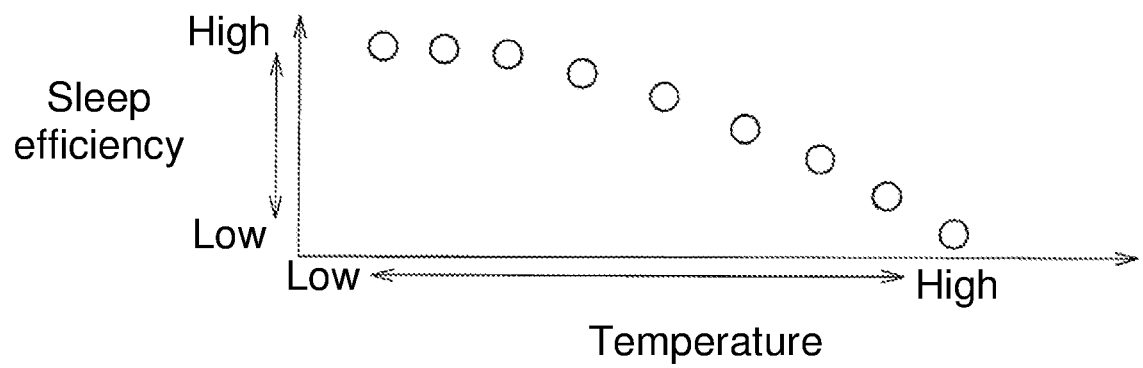
FIG. 3 illustrates views for explaining relevance between temperature and sleep efficiency.
Figure 3:
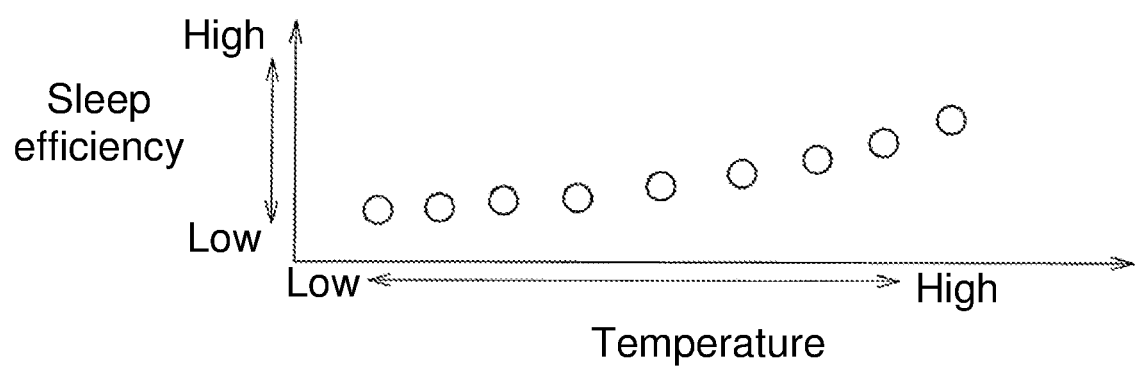
Figure 3:
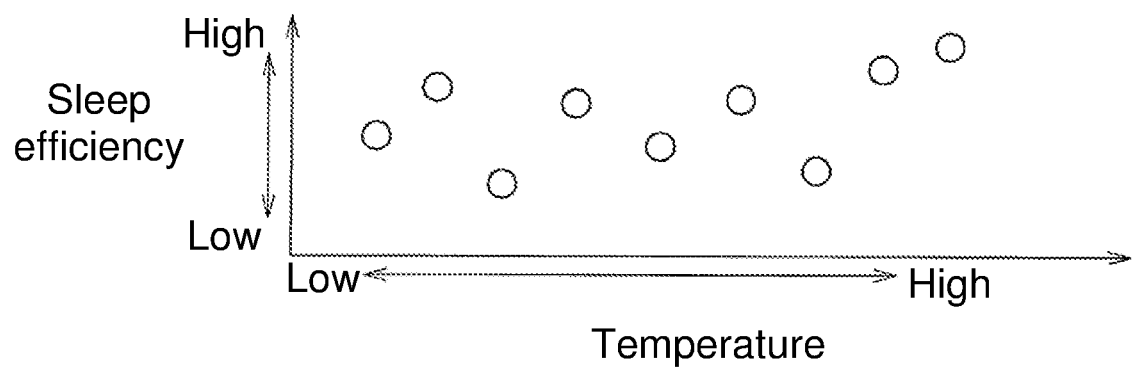

FIG. 3 illustrates views for explaining relevance between the sleep and the temperature, and FIGS. 3(a), 3(b), and 3(c) illustrate patterns having characteristic tendencies. An influence of the temperature on the sleep depends on a person, and the user belongs to one of the patterns in FIGS. 3(a) to 3(c).

Specifically, in the pattern of FIG. 3(a), the sleep efficiency is degraded with increasing temperature.

In the pattern of FIG. 3(b), the sleep efficiency is improved with increasing temperature.

In the pattern of FIG. 3(c), the sleep efficiency has no relevance to the temperature.

The sleep state predictor 23 extracts the relationship between the temperature and the sleep based on the past data of the user. A user pattern indicating the relevance between the temperature and the sleep efficiency is produced from the extracted past relationship between the temperature and the sleep as illustrated in FIGS. 3(a) to 3(c), and the sleep efficiency of the user is predicted from a night temperature on that day based on the pattern of the user.

Thus, the sleep efficiency of the user is predicted in consideration of the relevance between the temperature and the sleep, which depends on the user.

In the case that the past data of a target user is insufficiently stored, data of another user similar to the target user may be used. In this case, for example, a person whose sexuality, age, and sleep information are similar to those of the user is used among other users.

Even in this case, the data of another user is replaced with the data of the target user when the data of the target user is sufficiently stored.

The sleep state predictor 23 also predicts a scheduled wake-up time and a scheduled time in bed based on the past sleep information about the user, for example, daily, weekly, or monthly sleep information, and the predicted scheduled wake-up time and the predicted scheduled time in bed are used as prediction data. In the prediction processing, the user previously inputs the pieces of data of the wake-up time and time in bed, and the input pieces of data may be used as the prediction data.

Figure 4:
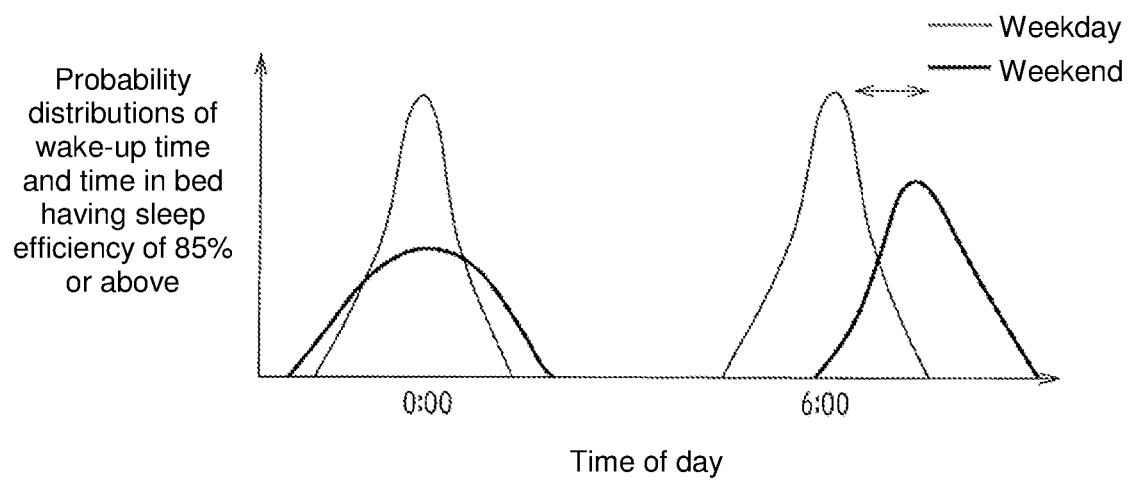
FIG. 4 is a view illustrating a method for extracting an optimal sleep time and an optimal sleep rhythm in the sleep improvement system of the embodiment, and is a probability distribution map illustrating a change in occurrence frequencies of user's wake-up and going-to-bed with respect to the time of day on a weekday and an weekend.
Figure 5:
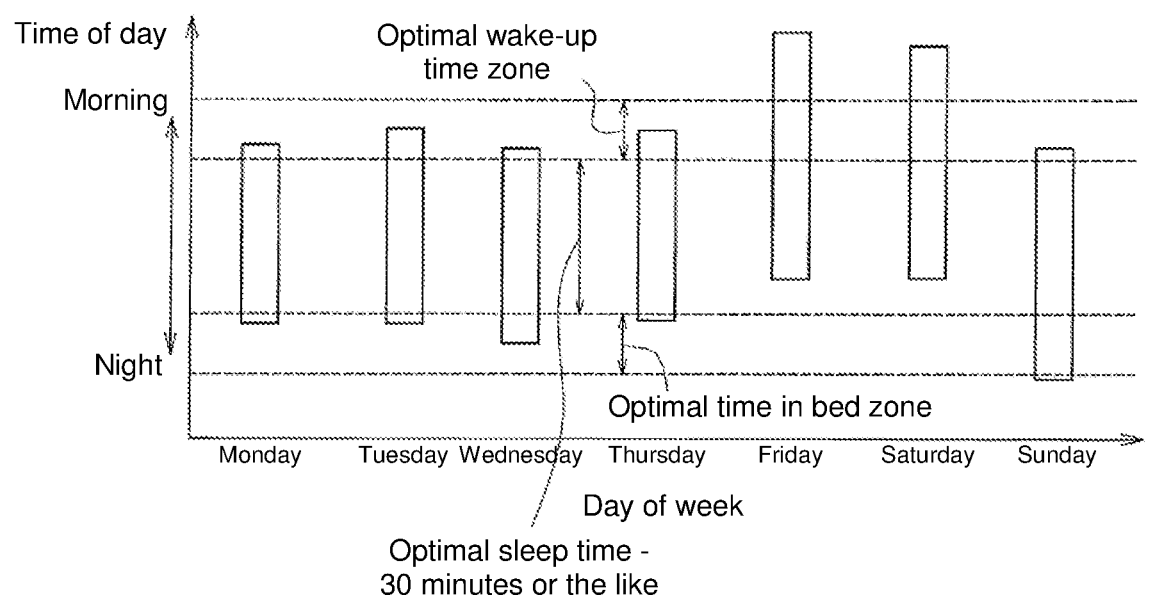
FIG. 5 is a view illustrating a method for extracting the optimal sleep time and the optimal sleep rhythm in the sleep improvement system of the embodiment, and is a view illustrating a sleep rhythm, an optimal wake-up time zone, and an optimal time in bed zone of one week.

The sleep state detector 25 extracts parameters such as the daily and/or weekly wake-up time, time in bed, sleep time, and sleep efficiency from the past sleep information about the user. Average values or data variations of these parameters are calculated with a dispersion as an index, and daily or weekly sleep state is extracted. FIGS. 4 and 5 illustrate specific examples of the sleep state.

FIG. 4 illustrates a probability distribution based on occurrence frequencies of the wake-up time and time in bed for a weekday and a weekend of the user when the sleep efficiency is larger than or equal to 85%. In the example of FIG. 4, the wake-up time on the weekend is later than that on weekdays.

The optimal sleep state calculator 24 extracts an optimal sleep time and an optimal sleep rhythm based on the daily or weekly sleep state.

As to a method for extracting the optimal sleep time, the sleep time having high subjective evaluation is used as the optimal sleep time. For example, the subjective evaluation means evaluation based on a questionnaire survey for users.

Alternatively, for a little difference between the weekday average sleep time and the weekend average sleep time, the average sleep time of the week is used as the optimal sleep time.

On the other hand, for a clear difference between the weekday average sleep time and the weekend average sleep time, the average sleep time on the day when the sleep efficiency of the week is larger than or equal to 85% is used as the optimal sleep time.

In the sleep state of FIG. 4, since the wake-up time on the weekend is later than that on weekdays, the sleep time of the user is estimated to be insufficient on the weekday. In this case, a level at which sleep quality of the user is not degraded, namely, the sleep time for which the sleep efficiency of 85% is maintained is calculated, and the calculated sleep time is used as the optimal sleep time.

FIG. 5 illustrates the sleep rhythm of the user, the optimal wake-up time zone of the user, and the optimal time in bed zone of the user for one week.

The sleep starts from the going-to-bed and ends by the wake-up. FIG. 5 illustrates a daily repetition of a series of sleep phenomena. The sleep rhythm means the going-to-bed timing and wake-up timing, between which the sleep time is maintained. As used herein, the optimal sleep rhythm means the going-to-bed timing and wake-up timing, between which the optimal sleep time is maintained.

The optimal wake-up time zone is set with a margin of 1 hour before and after the time the user wakes up on weekdays. The optimal time in bed zone is set with a margin of 1 hour before and after the time, at which the optimal sleep time is subtracted from the time the user wakes up on weekdays.

Thus, the optimal wake-up time zone and the optimal time in bed zone have the margin of 1 hour, and used as the recommended margin of the optimal wake-up time zone and the optimal time in bed zone, thereby extracting the optimal sleep rhythm.

In the example of FIG. 5, for Friday and Saturday, the time in bed and the wake-up time do not fall within the range of the optimal time in bed zone and the optimal wake-up zone, which deviate from the optimal sleep rhythm.

The sleep state evaluator 28 calculates "accumulation of the sleep time considered to be insufficient" on that day, namely, time in which a difference between the sleep time necessary for the user or the ideal sleep time for the user and the actual sleep time of the user is accumulated in a given period. The accumulated time is reflected on a message (to be described later).

Thus, the results of the sleep state detector 25, the sleep state predictor 23, and the optimal sleep state calculator 24 are reflected on the evaluation of the sleep state evaluator 28 as described above.

The message type selector 291 produces the message associated with the "accumulation of the sleep time considered to be insufficient" on that day. The message type selector 291 produces the message based on a difference from the optimal sleep rhythm calculated with the sleep state evaluator 28 or the data stored in daytime QOL evaluation database 13.

Desirably information indicating an evaluation content in terms of an index, such as subjective sleepiness in daytime, a fatigue degree, and disturbance of a biological clock, which is easy to understand, is produced as a message content.

At this point, the subjective sleepiness is obtained from a questionnaire such as "Did you have sleepiness today? How much sleepiness did you have?", and an answer such as "I had sleepiness. A sleepiness level was . . . " is reflected in the evaluation as daytime sleepiness information.

The message including the stress check result on that day may be produced as a sleep improvement index.

The message type selector 291 also produces the message associated with the "accumulation of the sleep time considered to be insufficient" on the next day. The "accumulation of the sleep time considered to be insufficient" on the next day is estimated in consideration of a deviation between the optimal information or prediction information about the sleep and the actual sleep information, the subjective sleepiness in daytime, and the like.

Additionally, a message including a variation in life pattern, a biological index such as a blood pressure and a weight, and the stress check result as an index indicating the sleep improvement may be produced.

A message associated with a recommended time in bed, a recommended wake-up time, a recommended behavior before the going-to-bed, or a recommended behavior after the wake-up is also produced. The message includes the recommended wake-up time, the recommended time in bed, and the behavior good for the sleep based on the result of the sleep state evaluator 28.

Preferably the message includes advice changed according to user's life pattern so as to encourage a person having a sufficient time before the going-to-bed to perform the recommended behavior before the going-to-bed, and so as to encourage a person having an insufficient time before the going-to-bed to perform the recommended behavior that is easy to do.

The message type selector 291 may produce the message content while the message content is in combination with various types of previously-produced messages. Table 1 illustrates the message types.

TABLE 1

| Type 1 | Type 2 | Type 3 |
|---|---|---|
| Communication | Greeting | Good morning. |
| | | . . . |
| | Weather information | It's fine weather today |
| | | . . . |
| | Local information | Cherry blossoms seem to have come out in your town. |
| | | . . . |
| | . . . | . . . |
| Information on current situation | Sleep state | You seem to have slept so well last night. |
| | | . . . |
| | Future sleep state prediction | You will not be able to sleep well because it will be hot next week. |
| | | . . . |
| | Lifestyle | You are good at getting up early. |
| | | . . . |
| | Living conditions | You have a lack of sleep. You seem to be busy. |
| | . . . | . . . |
| Information on recommended behavior | Information on gap between ideal and reality | Wake-up time has large variation of 2 hours. Ideal variation in wake-up time falls within 1 hour. . . . |
| | Optimal sleep state | You seem to have the most comfortable time when you get a 7-hour sleep. |
| | | . . . |
| | . . . | . . . |
| Feeling | Encouragement | Let's continue measurement at this pace. |
| | | . . . |
| | Sympathy | You should take a rest once in a while. |
| | | . . . |
| | . . . | . . . |

Table 2 illustrates output examples in the case that the message types in Table 1 are used.

TABLE 2

| <Message output example> | |
|---|---|
| Greeting: | Good morning. |
| Weather: | It's fine weather today. |

TABLE 2-continued

<Message output example>

| | |
|---|---|
| Sleep state: | You seem to have slept so well last night |
| Optimal sleep state: | You seem to have the most comfortable time when you get a 7-hour sleep. |
| Encouragement: | Let's continue measurement at this pace. |

The output message is stored in the message history database 15. The message history database 15 includes an output timing history, whether the message by the user is browsed or not, quality of the message in addition to the content of the output message. The user presses an input button for inputting information indicating "valuable for reference or not valuable for solution" after browsing the message, whereby the information about the quality of the message is obtained and stored.

The message timing selector 292 selects the message output timing based on the detection results of the lifestyle detector 26 and the living condition detector 27 or the information about the busyness estimated from the sleep information as described above.

Specifically, the message output timing is selected according to the user's lifestyle or situation such as the work day, the non-work day, and the busy period of the user.

For example, as to the wake-up time, the timing is selected for the user who wakes up early on the non-work day such that the message is early output, and the timing is selected for the user who wakes up late on the non-work day such that the message is output late.

Whether the selected message content is transmitted in the past is checked by the reference of the message history database 15. When there is a history that the selected message content is transmitted in the past, the selected message is set so as not to be output for a given period.

Therefore, when the message content to be output is identical to the past message content while is in the given period which the message is not output, the message is not output. When a time zone during which the user rarely browses the message by checking such the pieces of data as the output timing history and whether the message by the user is browsed is not, the message output timing is shifted such that the user easily browses the message.

The message outputting unit 30 outputs the message in the selected output timing when output of the selected message content is not prohibited.

The information about the content or timing of the output massage is stored as history data in the message history database 15.

[Outline of Sleep Improvement System According the an Embodiment]

Figure 6:
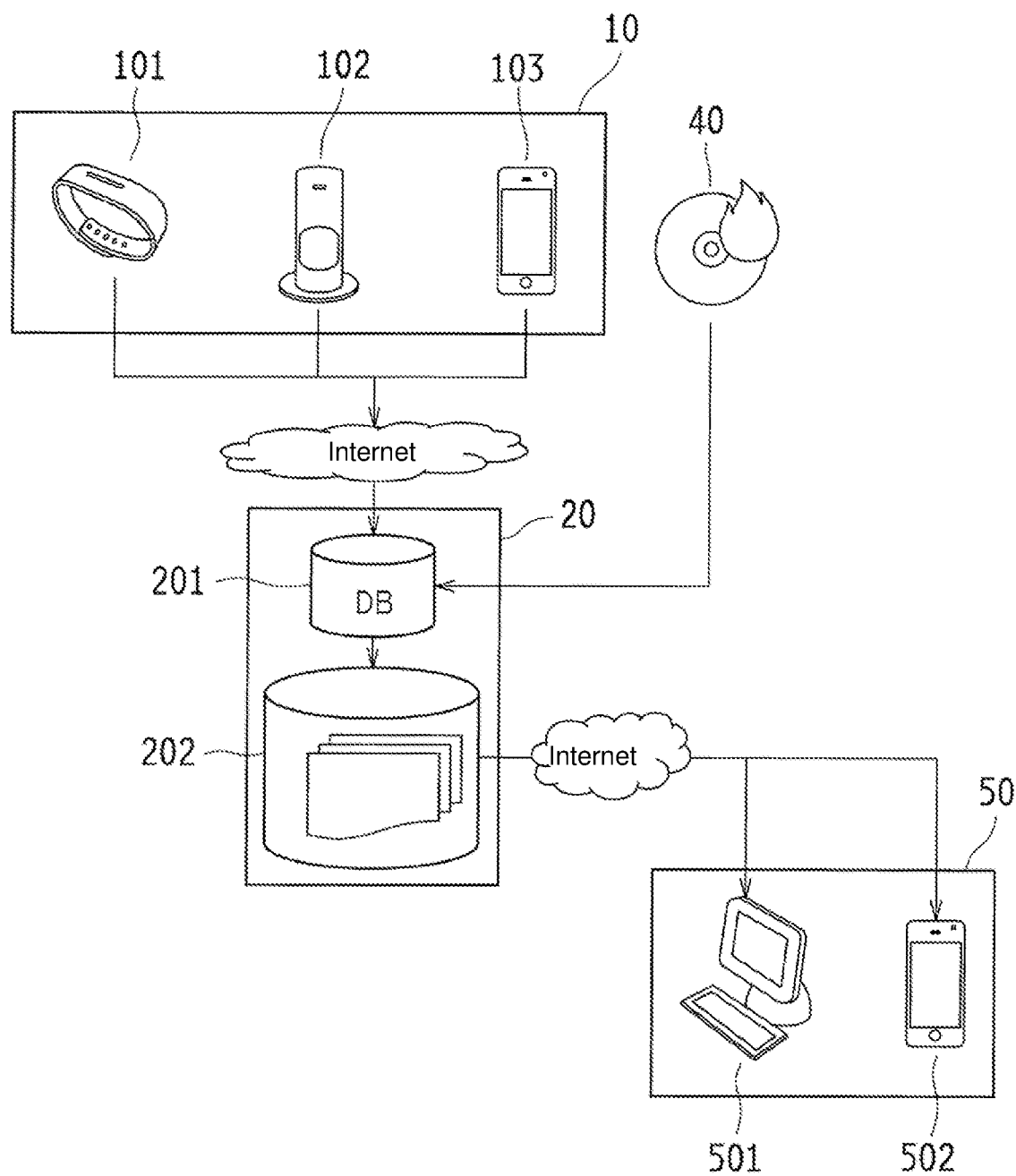
FIG. 6 is a view illustrating the sleep improvement system of the embodiment.

FIG. 6 is a view illustrating the sleep improvement system of the embodiment.

The sleep improvement system is constructed with a measurement device 10, an information storage and processing device 20, an information display device 50, and an external environment information system 40.

The measurement device 10 includes a device, such as a mobile terminal 103, to which the user directly input the information as necessary, a sleep information measurement device such as a sleep meter 102, and an activity information measurement device such as 24-H wearable terminal 101.

The sleep information such as the wake-up time, the time in bed, the total sleep time, the total time in bed, the sleep efficiency, the wake after sleep onset, the number of awakenings after sleep onset, and the sleep latency can be obtained with the sleep meter 102. The obtained sleep information is stored in the sleep information database 12 (see FIG. 1).

The 24-H wearable terminal 101 obtains user's behavior including user's daytime activity, for example, the number of steps and behavior information about a movement time. The obtained behavior information is stored in the daytime activity information database 14 (see FIG. 1).

The user can directly input the data using a mobile terminal 103. The input data is stored in the daytime QOL evaluation database 13 (see FIG. 1) or the sleep information database 12 (see FIG. 1).

The external environment information system 40 includes environment information such as weather data. The environment information is stored in the weather information database 11 (see FIG. 1).

Each device of the measurement device 10 includes a near-field radio communication function of transmitting the data of the measurement result by near-field radio communication in addition to a function of measuring index information.

Examples of the near-field radio communication function include, but not limited to, near field communication (NFC), communication by Felica (registered trademark), universal serial bus (USB) communication, and communication by Bluetooth (registered trademark).

The measured data or the data input by the user is transmitted to the information storage and processing device 20 through the Internet using the functions, and various pieces of data are stored in a predetermined database 201.

An information processing device 202 performs a series of pieces of processing of the blocks in FIG. 1 based on the pieces of data stored in the database 201. In the case that various messages are output, the message information is transmitted to the information display device 50 through the Internet. A personal computer 501, a smartphone 502, a tablet, and the like are properly used as the information display device 50.

The behavior information measurement device may include not only the sleep meter 102, but also another device. In this case, more information is obtained, and the state of the target user can more specifically be recognized.

[Effect of Sleep Improvement System According to the Embodiment]

The necessary sleep time or the quality of the sleep depends on an individual. Therefore, the evaluation and the sleep improvement message, which are obtained by the evaluation of the sleep state based on the data of the user, specifically, the sleep information data, the daytime QOL evaluation data, and the daytime activity information data, have high accuracy reflecting user's lifestyle or living conditions, and are satisfactory for the user. The information about the sleep improvement is output in timing suitable for the user, so that the user easily receives the information. Additionally, the user is satisfied of the provided recommended behavior, so that support can more effectively be given to the user to improve the sleep.

In the system of the embodiment, a person, such as a nurse, who is employed in shift work, or a person who has an irregular lifestyle can obtain the message information suitable for user's situation by previously inputting the work situation, namely, the behavior information with a personal computer.

Therefore, the system has a large effect on the person who is employed in the shift work, or the person who has the irregular lifestyle.

[Sleep Improvement Method According to the Embodiment]

A sleep improvement method of the embodiment will be described below with reference to FIG. 2 that is of a processing flowchart of the sleep improvement method and FIG. 1 that is of a block diagram of the sleep improvement system.

Whether the past sleep information about the user and the behavior information about the user are sufficiently stored is determined in obtaining each of the sleep information about the user, the behavior information about the user, the information about the daytime QOL evaluation information, and the environment information from the database (ST1). The data of the target user is required to a certain degree. For example, a data amount of one month, three months, or one year is enough for the obtainment. When the data is sufficiently stored, processing in step 3 (ST3) is performed using the data of the target user.

On the other hand, when the data is insufficiently stored, the information about another user similar to the user is obtained, and used as the information about the user. In this case, the information about another user whose sexuality, age, and sleep pattern are similar to those of the user is selected from the pieces of information about other users, and applied to the information about the target user (ST2), and processing in step 3 (ST3) is performed.

When the information about the target user is sufficiently stored, the information about another user is replaced with the information about the target user.

Then the sleep-associated information and the life-associated information are extracted (ST3).

Then, the sleep state predictor 23 extracts the relationship between the temperature and the sleep based on the past information about the user, and predicts the sleep efficiency of the user based on the temperature situation of the night on that day. The scheduled wake-up time and the scheduled time in bed are predicted based on the past sleep pattern about the user, for example, the daily, weekly, or monthly sleep pattern, and used as the prediction data (ST4).

The sleep state detector 25 extracts parameters such as the daily and/or weekly wake-up time, time in bed, sleep time, and sleep efficiency from the past sleep information data about the user, and detects the daily and weekly sleep patterns (ST5).

Then, the optimal sleep state calculator 24 calculates the user's optimal sleep time and the user's optimal sleep rhythm based on the daily and weekly sleep patterns extracted in ST5 (ST6). Because a method for extracting the optimal sleep time is similar to the configuration of the optimal sleep state calculator 24, the description is omitted.

Then, the lifestyle detector 26 and the living condition detector 27 estimate the holiday, the busyness, or the motivation for the maintenance and improvement of the lifestyle. Therefore, the living conditions of the user are detected (ST7).

Then, the sleep state evaluator 28 evaluates the deviation between the sleep information on that day and the optimal sleep information data. The sleep state evaluator 28 also performs the evaluation by calculating the deviation between the prediction information about the quality of the sleep, namely, the predictive values of the time in bed, wake-up time, and sleep time and the optimal sleep time and optimal sleep rhythm (ST8).

Then, the message is selected based on the calculation of the deviation and the evaluation. Specifically, the message associated with the accumulated sleep time considered to be insufficient is selected with respect to that day and the next day. The message type selector 291 selects the message content, and the message timing selector 292 selects the message timing. Because the selection of the message content and the selection of the message timing are already described in the message type selector 291 and the message timing selector 292, the description is omitted (ST9).

The message outputting unit 30 outputs the message in the selected output timing when the output of the selected message content is not prohibited (ST10).

The content or timing associated with the output message is stored in the history data (ST11).

Figure 2:
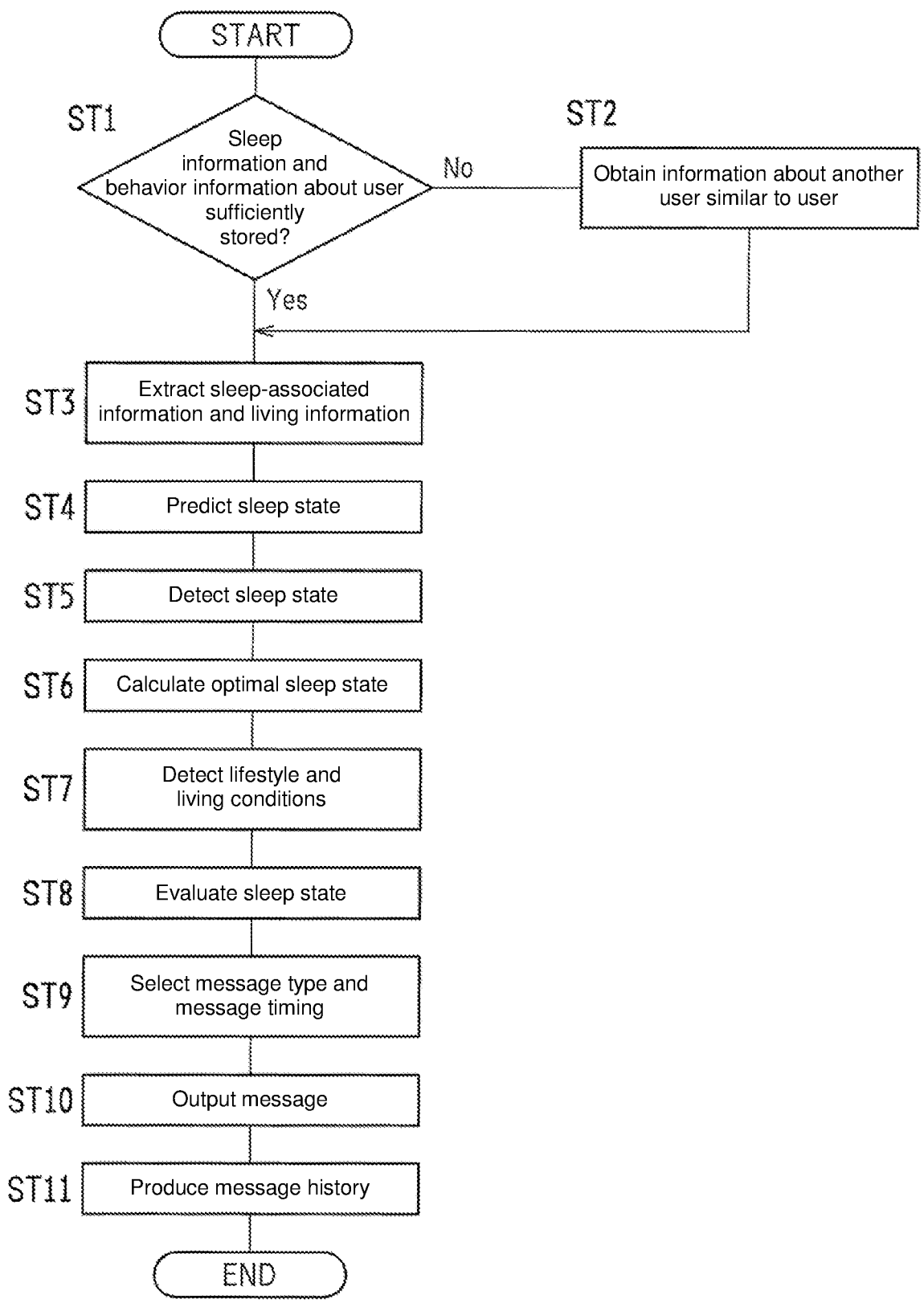
FIG. 2 is a flowchart illustrating processing of the sleep improvement system of the embodiment.

In the flowchart of FIG. 2, the order of the pieces of processing in steps 4 and 7 is not considered as long as the pieces of processing in steps 4 and 7 are performed before the processing in step 8.

DESCRIPTION OF SYMBOLS

1 database
11 weather information database
12 sleep information database
13 daytime QOL evaluation database
14 daytime activity information database
23 sleep state predictor
24 optimal sleep state calculator
25 sleep state detector
26 lifestyle detector
27 living condition detector
28 sleep state evaluator
291 message type selector
292 message timing selector
30 message outputting unit

The invention claimed is:

1. A sleep improvement system comprising a processor configured with a program to perform operations comprising:

retrieving, from a database, past sleep information about user sleep;

retrieving, from a weather information database, temperature data;

predicting a sleep efficiency, a sleep time, a going-to-bed time, and a wake-up time based on average values of the past sleep information and the temperature data, and a night temperature of a current day;

calculating a deviation between each of: the predicted sleep time and a weekend sleep time, the predicted sleep efficiency and a weekend sleep efficiency, the predicted going-to-bed time and an optimal going-to-bed time, and the predicted wake-up time and an optimal wake-up time;

selecting a type of sleep improvement message based on the calculated deviations;

selecting timing of outputting the selected type of the sleep improvement message, based on the past sleep information and data stored in a message history database indicating message timing and whether messages are browsed or not, so as to output the selected type of the sleep improvement message at a time at which the user is expected to browse the selected type of sleep improvement message; and outputting the selected type of sleep improvement message at the selected timing; and wherein:

the past sleep information comprises a relationship between the temperature data and sleep efficiency data.

2. The sleep improvement system according to claim 1, wherein the past sleep information further comprises at least one of: a past wake-up time; a past going-to-bed time; a past total sleep time; a past total time in bed; a past wake after sleep onset; a past number of awakenings after sleep onset; and a past sleep latency.

3. The sleep improvement system according to claim 1, wherein the processor is configured with the program to perform operations comprising evaluating an actual sleep efficiency, an actual sleep time, an actual going-to-bed time, and an actual wake-up time and calculating a deviation between each of: the actual sleep efficiency and the weekend sleep efficiency, the actual sleep time and the weekend sleep time, the actual going-to-bed time and the optimal going-to-bed time, and the actual wake-up time and the optimal wake-up time.

4. A sleep improvement method comprising:
  retrieving, from a database, past sleep information about user sleep;
  retrieving, from a weather information database, temperature data;
  predicting a sleep efficiency, a sleep time, a going-to-bed time, and a wake-up time based on average values of the past sleep information and the temperature data, and a night temperature of a current day; and
  calculating a deviation between each of: the predicted sleep time and a weekend sleep time, the predicted sleep efficiency and a weekend sleep efficiency, the predicted going-to-bed time and an optimal going-to-bed time, and the predicted wake-up time and an optimal wake-up time;
  selecting a type of sleep improvement message based on the calculated deviations;
  selecting timing of outputting the selected type of the sleep improvement message, based on the past sleep information and data stored in a message history database indicating message timing and whether messages are browsed or not, so as to output the selected type of the sleep improvement message at a time at which the user is expected to browse the selected type of sleep improvement message based on the data stored in the message history database; and
  outputting the selected type of the sleep improvement message in the selected timing; and
  wherein:
  the sleep information comprises a relationship between the temperature data and sleep efficiency data.

5. The sleep improvement method according to claim 4, wherein the past sleep information further comprises at least one of: a past wake-up time; a past going-to-bed time; a past total sleep time; a past total time in bed; a past wake after sleep onset; a past number of awakenings after sleep onset; and a past sleep latency.

6. The sleep improvement method according to claim 4, further comprising:
  evaluating an actual sleep efficiency, an actual sleep time, an actual going-to-bed time, and an actual wake-up time; and
  calculating a deviation between each of: the actual sleep efficiency and the weekend sleep efficiency, the actual sleep time and the weekend sleep time, the actual going-to-bed time and the optimal going-to-bed time, and the actual wake-up time and the optimal wake-up time.

* * * * *